(12) United States Patent  
Gabriel (10) Patent No.: US 6,173,199 B1  
(45) Date of Patent: Jan. 9, 2001

(54) METHOD AND APPARATUS FOR INTUBATION OF A PATIENT

(75) Inventor: Sabry Gabriel, Macon, GA (US)

(73) Assignee: Syncro Medical Innovations, Inc., Macon, GA (US)

( * ) Notice: Under 35 U.S.C. 154(b), the term of this patent shall be extended for 0 days.

(21) Appl. No.: 09/073,226

(22) Filed: May 5, 1998

(51) Int. Cl.$^7$ ............................................. A61B 5/05
(52) U.S. Cl. ................................ 600/424; 128/899
(58) Field of Search ........................... 600/424, 373; 128/899; 604/264, 270, 280; 324/260, 207.11, 207.13

(56) References Cited

U.S. PATENT DOCUMENTS

| | | | |
|---|---|---|---|
| 3,043,309 | 7/1962 | McCarthy | 128/348 |
| 3,674,014 | 7/1972 | Tillander | 128/2.05 R |
| 4,004,298 | 1/1977 | Freed | 3/1 |
| 4,024,855 | 5/1977 | Bucalo | 128/1 R |
| 4,063,561 | 12/1977 | McKenna . | |
| 4,077,412 | 3/1978 | Moossun | 128/347 |
| 4,114,601 | 9/1978 | Abels | 128/1 R |
| 4,134,405 | 1/1979 | Smit | 128/303 R |
| 4,336,806 | 6/1982 | Eldridge, Jr. | 128/348 |
| 4,338,937 | 7/1982 | Lerman | 128/283 |
| 4,416,289 | 11/1983 | Bresler | 128/737 |
| 4,431,005 | 2/1984 | McCormick | 128/656 |
| 4,593,687 | 6/1986 | Gray et al. | 128/200.26 |
| 4,717,631 | 1/1988 | Inoue et al. | 604/264 |
| 4,790,809 | 12/1988 | Kuntz | 604/8 |
| 4,850,963 | 7/1989 | Sparks et al. | 600/29 |
| 4,865,586 | 9/1989 | Hedberg | 604/93 |
| 4,913,139 | 4/1990 | Ballew | 128/200.11 |
| 4,943,770 | 7/1990 | Ashley-Rollman et al. | 324/207.17 |
| 5,005,592 | 4/1991 | Cartmell | 128/899 |
| 5,042,486 | * 8/1991 | Pfeiler et al. | 128/653 |
| 5,253,647 | * 10/1993 | Takahashi et al. | 128/653.1 |
| 5,257,636 | 11/1993 | White . | |
| 5,271,400 | 12/1993 | Dumoulin et al. | 128/653.2 |
| 5,273,025 | 12/1993 | Sakiyama et al. | 128/6 |
| 5,316,024 | 5/1994 | Hirschi et al. | 128/899 |
| 5,345,940 | * 9/1994 | Seward et al. | 128/662.06 |
| 5,353,807 | * 10/1994 | DeMarco | 128/772 |
| 5,386,828 | * 2/1995 | Owens et al. | 128/653.1 |
| 5,419,325 | 5/1995 | Dumoulin et al. | 128/653.2 |
| 5,425,367 | 6/1995 | Shapiro et al. | 128/653.1 |
| 5,431,640 | 7/1995 | Gabriel . | |
| 5,445,150 | 8/1995 | Dumoulin et al. | 128/653.1 |
| 5,492,538 | 2/1996 | Johlin, Jr. | 604/264 |
| 5,507,731 | 4/1996 | Hernandez et al. | 604/264 |
| 5,542,938 | 8/1996 | Avellanet et al. | 604/280 |
| 5,596,991 | * 1/1997 | Tanaka | 128/662.06 |
| 5,681,260 | * 10/1997 | Ueda et al. | 600/114 |
| 5,758,667 | * 6/1998 | Slettenmark | 128/899 |
| 5,902,238 | * 5/1999 | Golden et al. | 600/424 |
| 5,906,579 | * 5/1999 | Vander Salm et al. | 600/424 |

(List continued on next page.)

FOREIGN PATENT DOCUMENTS

WO 96/05768   2/1996   (WO) .
WO 96/32060   10/1996  (WO) .

*Primary Examiner*—Marvin M. Lateef
*Assistant Examiner*—Shawna J Shaw
(74) *Attorney, Agent, or Firm*—Arnall Golden & Gregory, LLP (57) ABSTRACT

A catheter having a distal end portion including a sensor responsive to the presence of a magnetic field or flux of a predetermined strength is provided. Also provided is a catheter system which further includes an external magnet. The sensor in the distal end portion is selected to respond when the distal end portion of the catheter is exposed to a magnetic field, such as provided by the external magnet, sufficient to capture and maneuver the distal end of the catheter. A catheter having a distal end portion that includes a steering portion for maneuvering the distal end of the catheter during intubation of a patient is also provided. A method for intubating a patient using the catheter systems provided, including an external magnet, is also disclosed.

32 Claims, 7 Drawing Sheets

U.S. PATENT DOCUMENTS 5,938,603 * 8/1999 Ponzi ................................. 600/424
5,997,473 * 12/1999 Taniguchi et al. ................... 600/117
6,007,478 * 12/1999 Siess et al. .............................. 600/16
6,015,414 * 1/2000 Werp et al. .......................... 606/108

* cited by examiner

METHOD AND APPARATUS FOR INTUBATION OF A PATIENT

BACKGROUND OF THE INVENTION

The present invention is generally in the area of medical catheters, and specifically to catheters constructed to facilitate guidance and placement of a distal end portion thereof at a predetermined site within the body of a patient.

A variety of methods for placing catheters and tubes in a patient's body are known. For example, enteral nutritional products can be delivered to a patient's gastrointestinal tract via a tube which is introduced through the naris of the patient's nose. The tube is advanced through the patient's esophagus and into the patient's stomach. In the event that it is preferable to deliver the enteral nutritional product directly to the patient's small bowel, the tube is further advanced beyond the pylorus into the patient's duodenum or small bowel. However, advancement of the tube into the patient's duodenum can be difficult in many patients. One method for advancing a tube through the stomach and into the duodenum entails the use of the natural peristaltic movement of the gastrointestinal tract. Such advancement may require as long as three to five days in some patients. Pharmaceutical products can be used in order to enhance the peristaltic action within the gastrointestinal tract and thereby decrease the time required to advance the feeding tube into the small bowel.

Serial X-rays typically are used to determine the location of the distal end of the tube as it advances by peristaltic action through the pylorus to the duodenum, thereby exposing the patient repeatedly to radiation and increasing the costs associated with placement of the tube. For these reasons, the use of naturally occurring or pharmaceutically enhanced peristalsis provides a sub-optimal method for placing a tube in a patient's small bowel.

It is known in the art to use magnetic flux or a magnetic field in the placement of catheters in the gastrointestinal tract. For example, U.S. Pat. No. 3,043,309 to McCarty describes the use of a localized magnetic field generated by an electrical magnet to manipulate a suction tube having a magnetic member at its distal end. The suction tube is constructed to be manipulated through an intestinal obstruction. The electrical magnet enables a medical professional to turn off the magnet when using fluoroscopy radiation to determine the precise location of the distal end of the tube. Without the ability to deactivate the magnetic field in this manner, the field would distort the image on the fluoroscopy screen, thereby preventing a precise determination of the location of the distal end of the tube.

U.S. Pat. No. 3,794,041 to Frei, et al. discloses beads of a ferromagnetic material constructed to be inserted in a body part with a catheter for moving the body part using an external magnet. U.S. Pat. No. 3,847,157 to Caillouette, et al. discloses the use of a magnetic indicator in a medico-surgical tube to identify the location of a tube containing a ferromagnetic material. U.S. Pat. No. 3,674,014 to Tillander discloses a distal end portion of a catheter having a plurality of magnetic tubular elements with ball-shaped ends to allow deflection of the sections with respect to each other for guidance of the catheter distal end. U.S. Pat. Nos. 3,961,632 and 4,077,412 to Moossun disclose a trans-abdominal stomach catheters of the Foley type used to direct the placement of the catheter by way of an external puncture from outside the abdomen through the stomach wall. U.S. Pat. No. 3,358,676 to Frei, et al. shows the use of magnets for remotely controlling propulsion of a magnet-containing beads through a duct of a human.

U.S. Pat. No. 5,431,640 to Gabriel discloses the use an external magnet to establish a magnetic field for permeating body tissue and enveloping the lesser curvature of the stomach for magnetic direction of a distal end of a catheter feeding tube having a permanent magnet associated therewith. The presence of the permanent magnet on the distal end portion of the catheter tube presents the advantage of steering the catheter magnet by the external magnet.

Maneuvering a catheter to the distal duodenum of a patient using the magnetic field produced by an external magnet requires precise knowledge of the anatomy of the stomach and duodenum in relation to the abdominal surface of a patient. This knowledge is necessary so that the operator can maneuver the external magnet over the abdomen of the patient in a precise path resulting in advancement of the catheter through the stomach and into the duodenum of the patient. An operator maneuvering an external magnet cannot see through the abdominal wall to decide whether the distal end portion of the catheter is continuously captured by the magnetic field of the external magnet during the advancement of the catheter. Thus, an additional procedure is required to determine whether the distal end of the catheter is properly advancing into the patient's duodenum. One method discussed previously and having apparent shortcomings involves the use of X-ray monitoring to confirm the position of the distal end of the catheter. An alternative method, described in U.S. Pat. No. 5,431,640, entails the aspiration of fluid from the distal end of the catheter and the measurement of the pH of the aspirated fluid. However, pH values for a particular individual may vary from expected values, as occasionally occurs in response to medications, thereby resulting in false position information. What is needed is an apparatus and method for advancing the distal end portion of a catheter using the field of an external magnet which provides an indication whether the catheter distal end is captured by the external magnet, thereby indicating whether the distal end of the catheter is being properly advanced into the patient's duodenum.

It is an object of the present invention to provide catheters which are more easily and accurately positioned than the catheters currently available.

SUMMARY OF THE INVENTION

A catheter having a distal end portion preferably including a sensor responsive to the presence of a magnetic field or flux of a predetermined strength is provided. Also provided is a catheter system which further includes an external magnet. The sensor in the distal end portion is selected to respond when the distal end portion of the catheter is exposed to a magnetic field, such as provided by the external magnet, sufficient to capture and maneuver the distal end of the catheter.

The catheter system further includes a catheter having a distal end portion that includes a steering portion for maneuvering the distal end of the catheter during intubation of a patient. In one embodiment, the steering portion takes the form of a portion provided with increased flexibility as compared with the flexibility of an adjacent portion of the distal end portion of the catheter. In another embodiment, the catheter system further includes a catheter having a distal end portion that includes a steering portion having an asymmetrical projection which facilitates advancement of the catheter as it encounters surfaces that are substantially perpendicular to its direction of advancement.

Also provided is a method for intubating a patient including the use of a catheter system as disclosed herein with an external magnet. The catheter is placed in a portion of a patient's body, and the external magnet is brought into proximity of the distal end portion of the catheter such that the sensor indicates that the distal end portion of the tube has been captured by the external magnet. The external magnet is then used to position the distal end portion of the catheter in a selected position within the patient's body. The method may also be used with the catheter having a distal end portion that includes a steering portion and using the steering portion to maneuver the distal end portion of the catheter during intubation of the patient. The catheter may also be adapted for insertion within the vasculature of a patient, with or without the use of the sensor.

DETAILED DESCRIPTION OF THE INVENTION

Catheters

Figure 1:
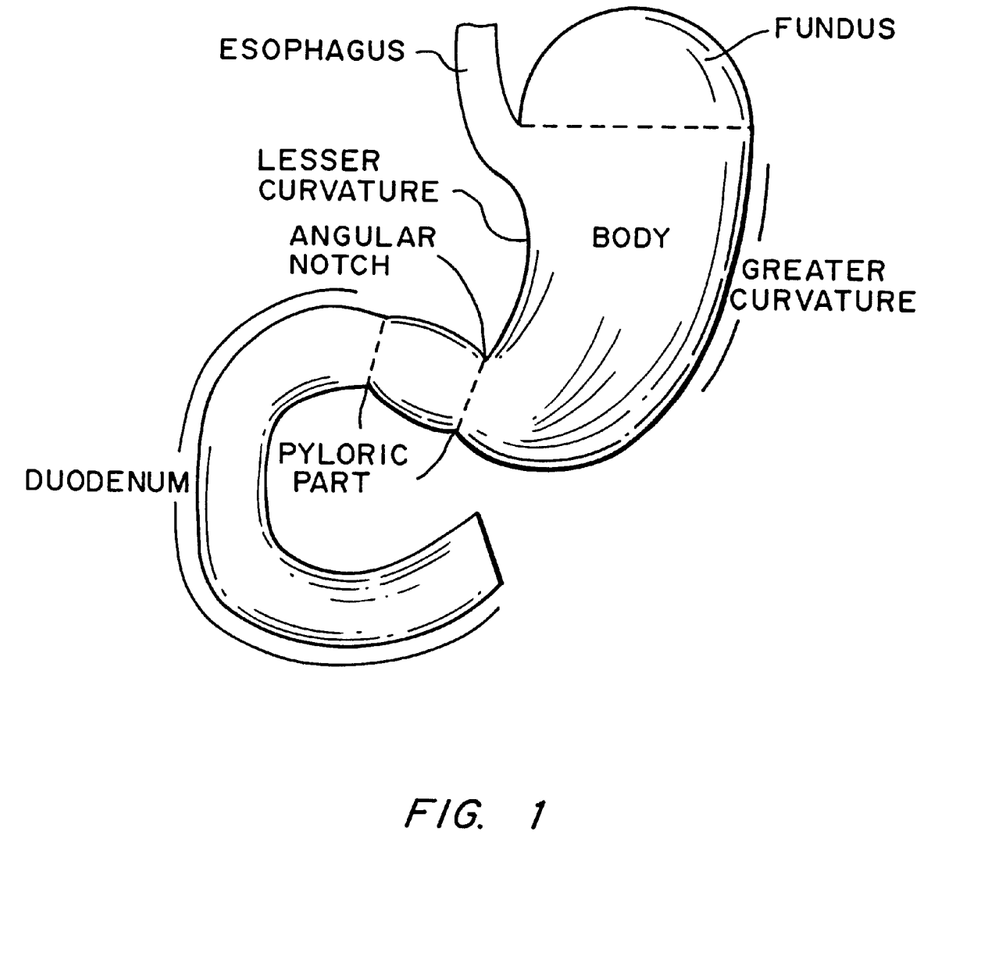
FIG. 1 is a schematic illustration of the anatomical configuration of the stomach and duodenum through which the catheter of the present invention is navigated.

In a preferred embodiment of the catheter disclosed herein, the distal portion of the catheter must be navigated through the stomach and placed in the duodenum so that nutrition or medication can be delivered directly into the small intestine. The anatomical configuration of the stomach is illustrated in FIG. 1, with salient features of the stomach and associated esophagus and duodenum labeled.

Figure 2:
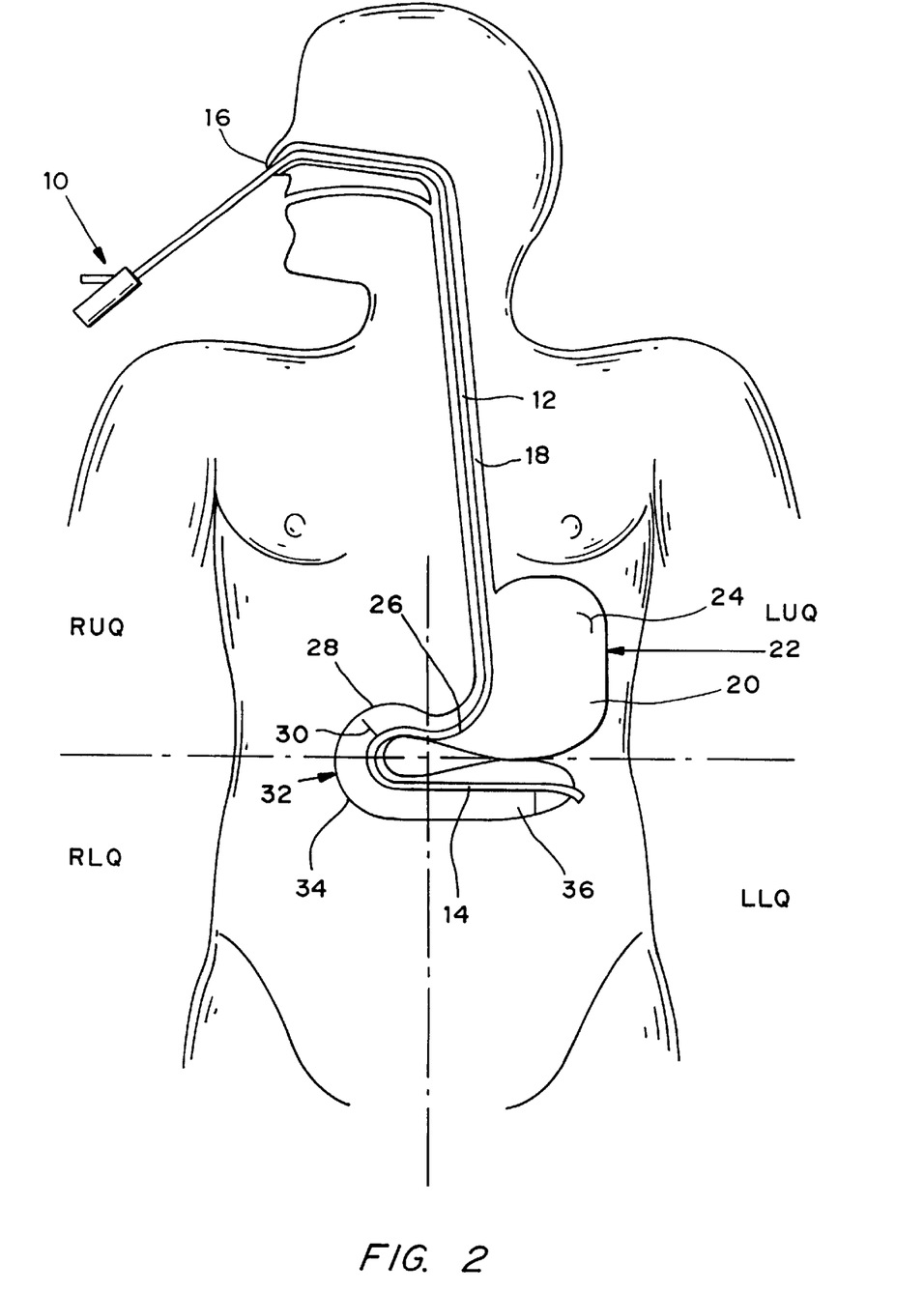
FIG. 2 is a schematic illustration of a patient showing a catheter feeding tube in place through the naris of the nose to deliver nutrition or medication directly into the small intestine.

One embodiment of the catheter system is illustrated in FIG. 2, wherein catheter 10 has a catheter body portion 12 which is elongated and extends to a distal end portion 14 for delivery of nutrition or medication. It will be appreciated that catheter 10 can be used to deliver various fluids to a variety of locations within a patient's body. For the purposes of this disclosure, reference will be made to use of catheter 10 to deliver an enteral nutritional product to a patient's duodenum. However, it will be appreciated that the present invention is not limited to this application; other embodiments are described below.

The distal end portion 14 of the catheter 10 is introduced through the naris 16 of the nose and advanced by the application of a longitudinally compressive force to the catheter 10, thus urging distal end portion 14 in the direction of the backward portion of the patient's head and thence to the esophagus 18. Preferably, the distal end portion 14 of the catheter 10 is coated with a lubricant while a numbing agent is applied to the nasal mucosa. The passageway of the esophagus affords ample guidance to the distal end portion 14 of the catheter 10 when it enters the stomach body portion 20 of the stomach 22 at the lower portion of the fundus 24. The movement of the distal end portion 14 along the esophagus and into the body of the stomach occurs within the left upper quadrant ("LUQ").

The stomach 22 has a generally J-shaped configuration. The largest transverse anatomical size of stomach 22 is located at the cardiac orifice, i.e., the site at which the esophagus enters the stomach. The transverse dimension of the stomach narrows moving away from the cardiac orifice in the direction of the normal passage of food through the gastrointestinal tract. An angular notch 26 is present at the border between the left upper quadrant ("LUQ") and the right upper quadrant ("RUQ"). From the angular notch, there commences a smaller transverse dimension at the pyloric part 28 typically residing in the right upper quadrant ("RUQ") with pyloric sphincter 30. The pyloric sphincter 30 is a muscular closure which dilates to permit the passage of food from the stomach 22 into the small bowel 32. The small bowel 32 includes a duodenum 34 and the distal duodenum 36. Food passes through the pyloric sphincter 30 into the duodenum 34, the duodenum 34 extending to the right lower quadrant ("RLQ") and then in a general horizontal direction into the left lower quadrant ("LLQ") where the distal duodenum 36 of the small intestine is situated.

The generally J-shaped configuration of the stomach 22 is arranged with the longer limb of the "J" lying to the left of the median plane and the major part in the left upper quadrant ("LUQ"). The long axis of the stomach passes downwardly, forwardly, and then to the right and finally backwardly and slightly upwardly. The size and shape of the stomach 22 vary greatly from patient to patient, for example, in short, obese persons the stomach is high and transverse whereas in tall persons the stomach is elongated. It is known that in a given patient the shape of the stomach depends on whether the stomach is empty or full, the position of the patient, and the phase of respiration. At the cardiac orifice, an acute angle is formed which tends to misdirect the distal end of the catheter toward the fundus 24 rather than toward the pyloric part 28 as the catheter is urged through the stomach.

Figure 3:
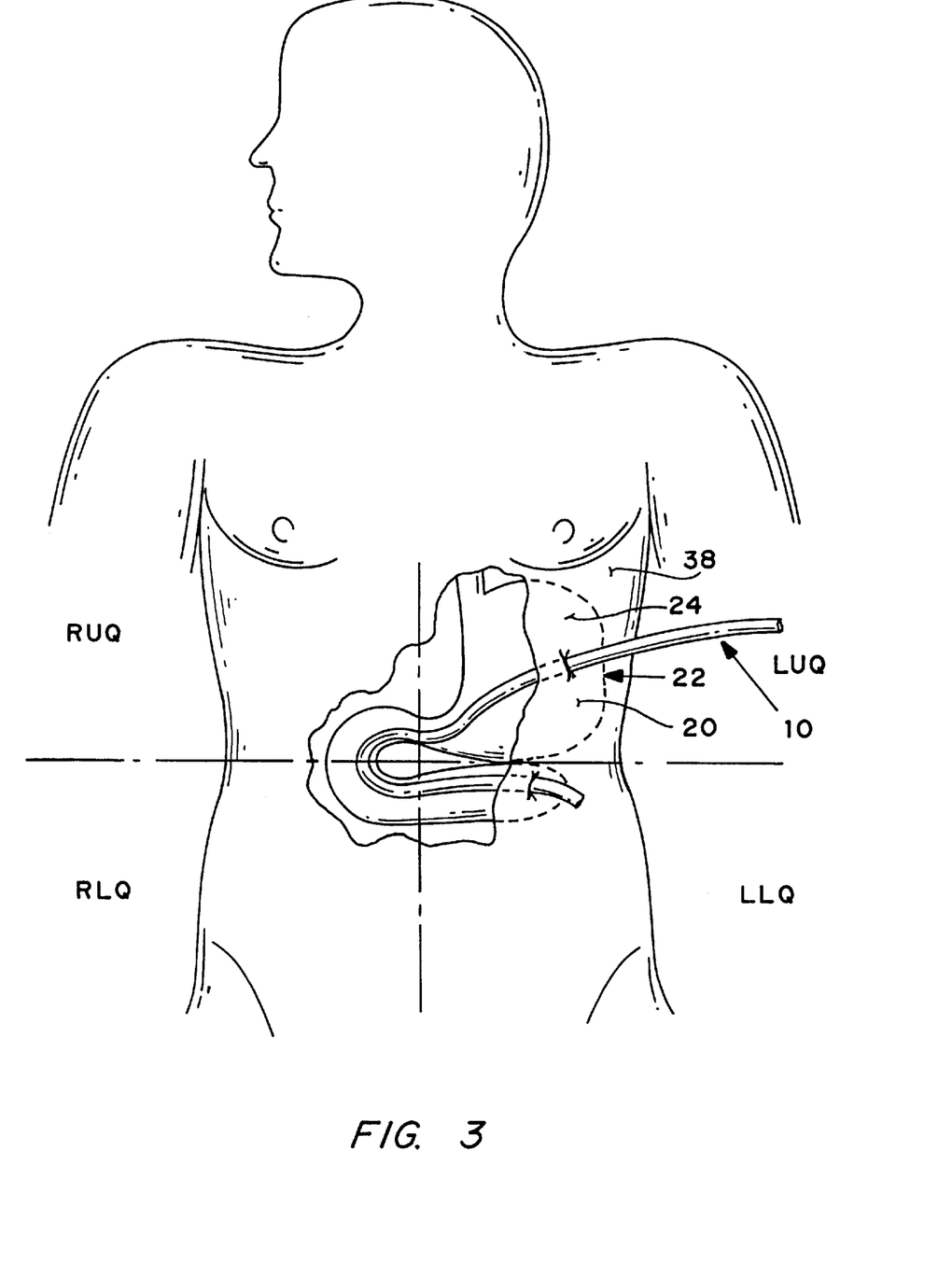
FIG. 3 is a schematic illustration of a patient showing a catheter feeding tube in place through the abdominal wall to deliver nutrition or medication directly into the small intestine.

An alternative entry site to the stomach 22 for the catheter 10 is illustrated in FIG. 3. The distal end of the catheter enters through a stoma tract in the patient's abdominal wall 38 to the stomach body portion 20 of the stomach 22 rather than through the naris of the nose. This stomach formation technique is well known in the art and is referred to as percutaneous endoscopic gastrostomy ("PEG"). Alternatively, the catheter 10 can be placed through a stoma tract in the patient's abdominal wall 38 directly into the patient's duodenum or jejunum. The apparatus and method of placement of the present invention are particularly suited for use in placing a feeding tube through a stoma tract formed through the patient's abdominal wall by a PEG procedure and in placing a feeding tube through the patient's nose.

Figure 4:
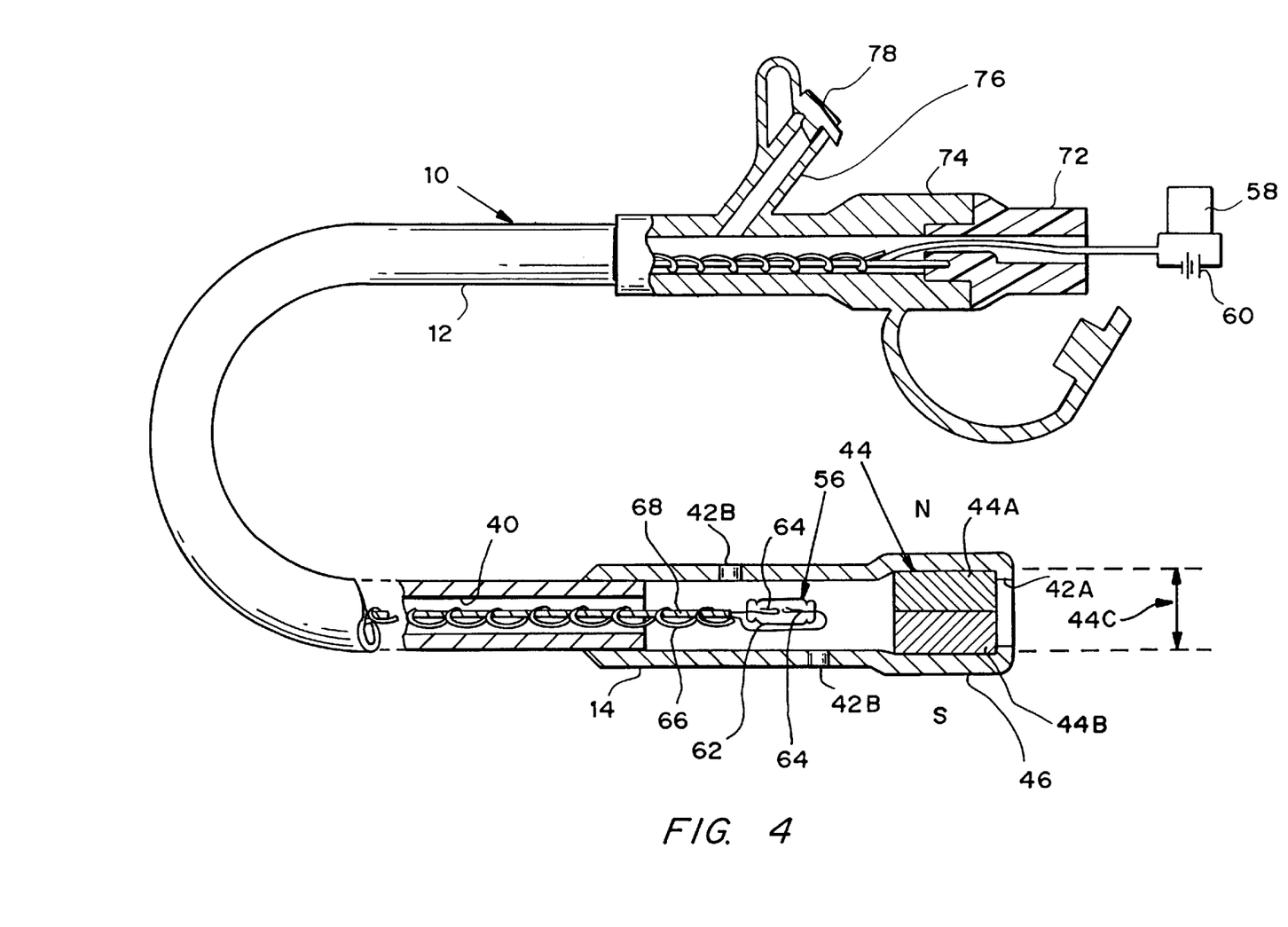
FIG. 4 is an enlarged plan view, partly in section, of a catheter according to the present invention in which the distal end portion includes a permanent magnet arranged such that lines of flux will travel from a first side of the catheter to an opposite side.

One embodiment of the catheter disclosed herein is shown in FIG. 4, enlarged to illustrate catheter 10 in greater detail. When the catheter 10 is configured as a feeding tube, the catheter 10 is about 50 inches long. Catheter body portion 12 typically has a diameter of about 3 mm and can be constructed in whole or in part of a radiopaque material in order to facilitate identification thereof using known X-ray techniques. The distal end portion 14 of the catheter 10 typically has an outside diameter of about 5 mm. The distal end portion 14 can be integrally form ed with the remainder of catheter body portion 12. Alternatively, distal end portion 14 can be mounted mechanically on, or chemically bonded to, the remainder of catheter body portion 12. A lumen 40 in the catheter body portion 12 is in fluid communication with an external environment of distal end portion 14 through one or more apertures. The aperture can be defined as an axial orifice 42A at the terminal end of distal end portion 14. The apertures also can be defined through the walls of distal end portion 14 as eyelets 42B. The apertures allow a fluid to be directed through lumen 40 and into the site in which the distal end portion 14 of catheter 10 is positioned.

Magnetically Responsive Elements

The catheter is provided with a magnetically responsive member at distal end portion 14. In a first embodiment of the present invention, the magnetically responsive member includes a cylindrically shaped permanent magnet 44 positioned in distal end portion 14 of catheter 10. The magnetically responsive member can alternatively be constructed of a ferromagnetic material, i.e., a material in which a magnetic state can be induced. Permanent magnet 44 in the embodiment of FIG. 4 has a diameter of about 5 mm and a length of about 6 mm. A slight bulge 46 in the lumen 40 occurs when the permanent magnet 44 is inserted through axial orifice 42A. In an alternative configuration, permanent magnet 44 is placed on an exterior wall of distal end portion 14. The permanent magnet 44 can include opposite, hemi-cylindrical pole faces 44A and 44B which exhibit polarization across a diameter 44C such that lines of magnetic flux travel from hemi-cylindrical pole 44A to hemi-cylindrical pole 44B.

Figure 5:
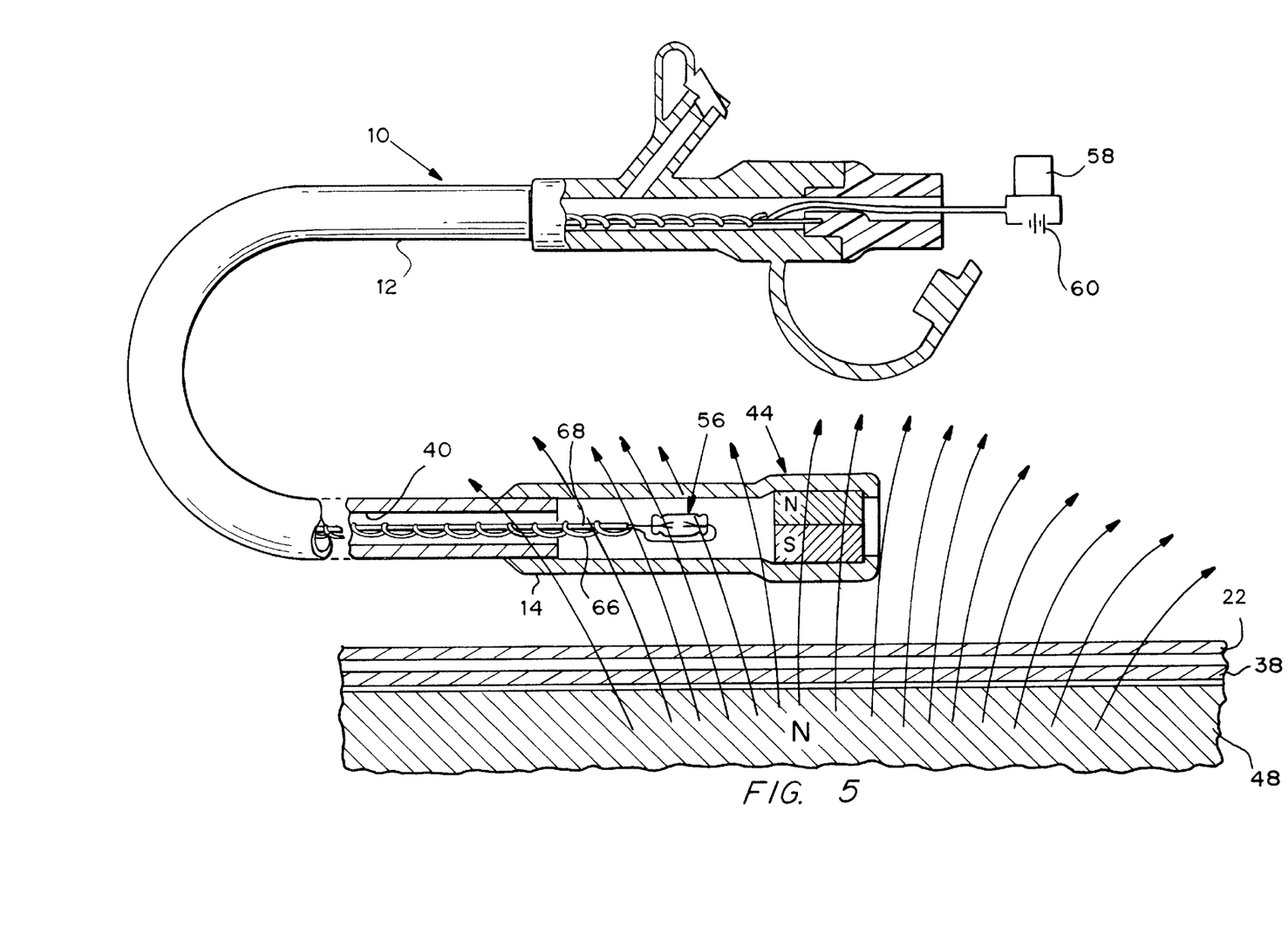
FIG. 5 is an enlarged plan view, partly in section, showing the distal end of the catheter of FIG. 4 in the proximity of an external magnet.

An external magnet 48 is illustrated in FIG. 5 in a proximal relation with the distal end portion 14 of the catheter which encounters the magnetic field of the external magnet. The wall of the stomach 22 and the abdominal wall 38 are between the distal end portion 14 of the catheter 10 and the external magnet 48. The inclusion of the permanent magnet 44 polarized along the diameter, as illustrated, results in the orientation of the distal end portion 14 transversely with respect to the external magnet 48 when the field of the external magnet has captured the permanent magnet 44 in the distal end portion 14. This is favorable for guiding the catheter through the curves of the gastrointestinal tract.

Figure 6:
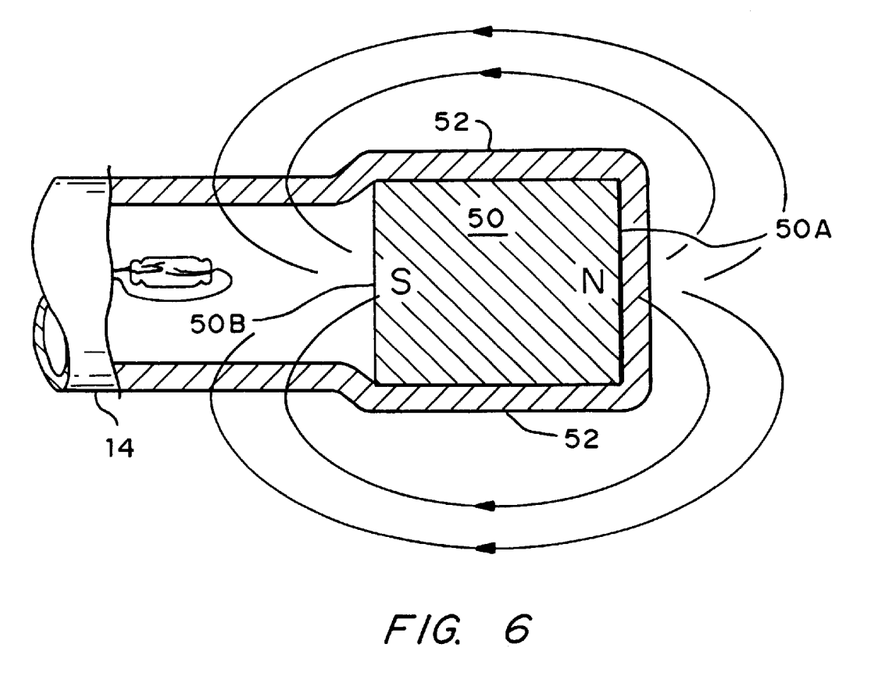
FIG. 6 is an enlarged sectional view of the distal end portion of a catheter according the present invention having a permanent magnet in the distal end portion, which is differently arranged than the magnet in the catheter tip of FIG. 4 such that the lines of flux travel from a generally planar face of the magnet adjacent the terminal end of the catheter to an opposite generally planar face of the magnet.
Figure 7:
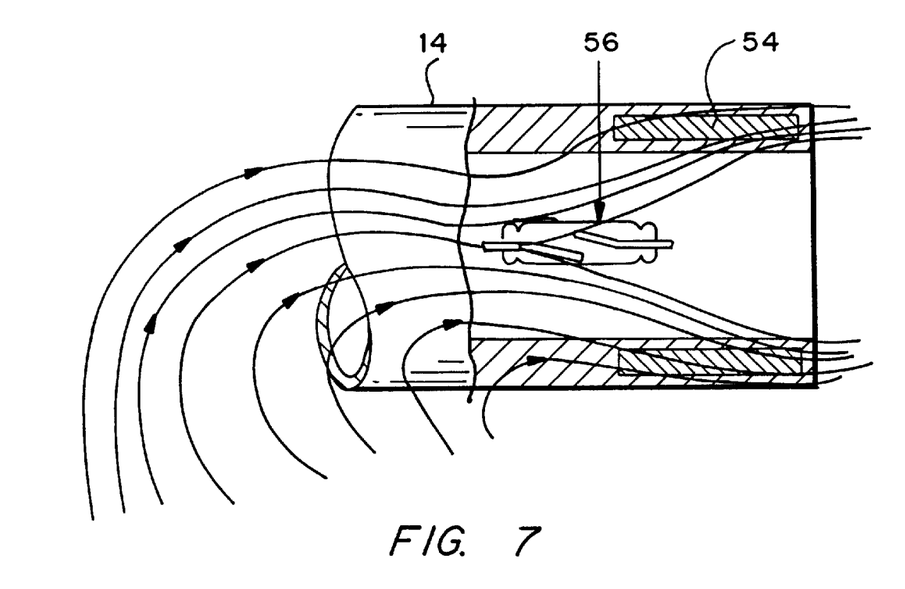
FIG. 7 is an enlarged sectional view of the distal end portion of a catheter according to the present invention having a ferromagnetic tubular member in the distal end portion.

In an alternative embodiment, the magnetically responsive member is a permanent magnet 50 arranged in the distal end portion 14 of the catheter 10 as illustrated in FIG. 6. Permanent magnet 50 is constructed with a cylindrical surface between opposing planar pole faces. The permanent magnet 50 is supported in the lumen 40 with the cylindrical surface producing a slight bulge identified by reference numeral 52. The permanent magnet 50 inserted through axial orifice 42A is distinctly polarized when compared with the permanent magnet 44 illustrated in FIGS. 4 and 5. The lines of flux of permanent magnet 50 in FIG. 6 extend from a first generally planar pole face 50A adjacent a terminal end of the catheter to an opposite second generally planar pole face 50B. As described hereinbefore, the magnetically responsive member can take the form of a ferromagnetic insert 54 in the distal end portion 14 of the catheter as illustrated in FIG. 7. According to this embodiment of the catheter system disclosed herein, the ferromagnetic insert 54 is tubular in cross-section. The insert can be encapsulated within the catheter wall at the distal end portion 14 or can be provided on an interior surface of lumen 40 or an external surface of distal end portion 14. It has been found that the selection of an external magnet can be made so as to provide a magnetic field strength sufficient to induce magnetization in the ferromagnetic insert 54. The induced magnetization provides a magnetic coupling between the external magnet and the ferromagnetic insert 54, thus allowing the distal end portion 14 to be manipulated by movement of the external magnet.

The material comprising ferromagnetic insert 54 can be an alloy which is defined as a ferromagnetic alloy that becomes magnetized readily upon application of a field and that resumes practically a nonmagnetic condition when a field is removed. Suitable ferromagnetic materials include, but are not necessarily limited to, permandure, iron, iron silicone steel, iron cobalt alloys, and iron nickel alloys. The magnetization of ferromagnetic insert 54 which occurs in the presence of the applied field by the external magnet is defined as the induced magnetization and is distinguished from permanent magnetization which is present without an applied field.

Sensors

Sensor 56 is positioned at distal end portion 14 of the catheter 10. Sensor 56 can be integral with or attached to catheter 10, or can be positioned on a stylet 68 inserted into catheter 10. The sensor 56 is preferably constructed to detect the presence of a magnetic field of a predetermined magnitude. The magnetic field can be either the result of the magnetic flux of the external magnet 48 or the induced magnetism of ferromagnetic insert 54, or a combination thereof. The predetermined magnitude of the magnetic field is selected to be sufficient to ensure that permanent magnet 44, 50 or ferromagnetic insert 54 is magnetically coupled to the external magnet. Sensor 56 preferably is constructed to provide an audio, visual, or tactile indication through indicator 58 when the threshold magnetic field is present at distal end portion 14. In the embodiments in which permanent magnets 44 and 50 are provided on distal end portion 14 of the catheter 10, sensor 56 is constructed such that it does not respond to the magnetic field or magnetic flux density of permanent magnets 44 and 50. In FIGS. 5 and 6, sensor 56 is spaced from the permanent magnet 44 and 50 in the distal end portion 14 of the catheter in order to avoid false triggering of sensor 56. Sensor 56 can have any of a variety of forms utilizing principles of operation well known in the art to respond to the presence of a magnetic field or a magnetic flux of a predetermined magnitude.

As described above, sensor 56 preferably is constructed to provide an indication of the presence of a threshold magnetic flux or field at distal end portion 14. In the embodiment of the catheter system depicted in FIG. 4, sensor 56 is connected to an audio or visual signal generator 58 and a power supply 60. In this embodiment, sensor 56 includes an envelope 62 forming a protective housing containing electrically conductive limbs consisting of leaf-like reeds 64 having a predetermined elasticity such that the electrical state of the sensor 56 changes in response to the presence of the magnetic field or flux at the predetermined threshold level. The electrically conductive leaf-like reeds 64 extend from opposite ends of the envelope 62 in a spaced apart and overlying relation. In the embodiment of FIG. 4, the leaf-like reeds are constructed such that they are out of electrical contact with one another in the absence of a magnetic field or magnetic flux of a predetermined magnitude. However, the leaf-like reeds are elastically forced into electrical contact with one another in the presence of a magnetic field or magnetic flux of sufficient strength to provide a magnetic coupling between the external magnet and the distal end portion 14, thereby allowing electricity to flow through the sensor 56 and actuate a signal generator 58. Movement of the leaf-like reeds 64 between their electrical contact and separated positions is responsive to the presence or absence of a magnetic field or magnetic flux.

Signal Generators

Signal generator 58 preferably is positioned external to the patient during placement of catheter 10. The requisite electrical connection between sensor 56 and signal generator 58 can be achieved using a variety of known technologies. For example, electrically insulated wire 66 can be wrapped around stylet 68, with wire 66 providing an electrical coupling between sensor 56 and signal generator 58. In an alternative embodiment, stylet 68 can be formed of an electrically conductive material which provides the requisite electrical coupling between sensor 56 and signal generator 58. Electrical insulators preferably are provided around stylet 68 in order to prevent the inadvertent delivery of an electrical shock to the patient.

The signal generator 58 is preferably a light bulb or other visual signal which provides a detectable signal indicating that sensor 56 is detecting a threshold level of a magnetic field or magnetic flux. A physician is thereby informed that distal end portion 14 of catheter 10 has been captured by external magnet 48 and that the external magnet 48 can be used for manipulating the distal end portion 14 of the catheter 10. An audible signal emitted by a buzzer or bell, for example, may be used instead of a light bulb without departing from the present invention. A vibrating element could also be provided in order to provide a tactile signal indicating that the requisite magnetic coupling is present.

Figure 8:
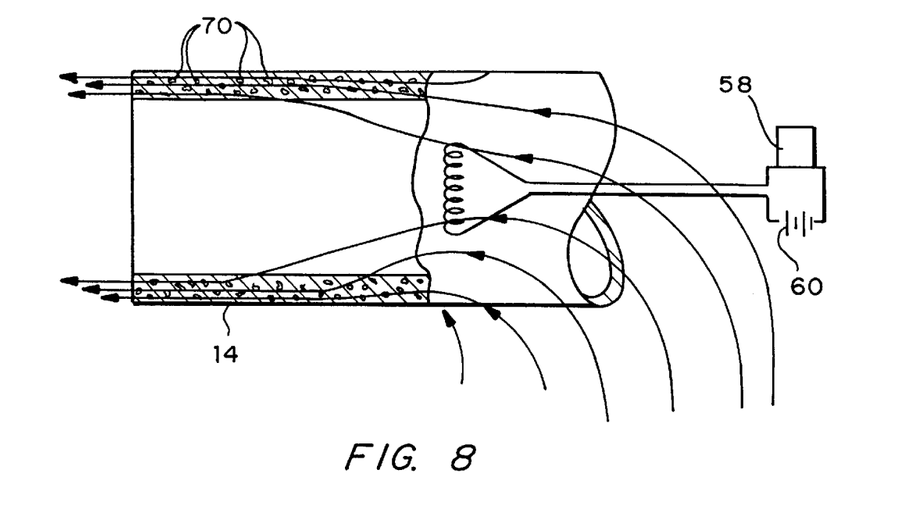
FIG. 8 is an enlarged sectional view of the distal end portion of a catheter according to the present invention having bits of ferromagnetic material embedded in the distal end portion to magnetically respond to a magnetic field of an external magnet.

A further embodiment of a ferromagnetic insert in the distal end portion 14 of a catheter is illustrated in FIG. 8 The distal end portion of the catheter includes a plurality of bits 70 consisting of a ferromagnetic material. The bits 70 are embedded in the wall of the distal end portion 14 of the catheter wall material as a matrix. Magnetic flux from the external magnet 48 will be drawn to the bits 70 embedded in the catheter, thereby increasing the flux density and inducing magnetization within bits 70. The induced magnetization functions as described in regard to the ferromagnetic insert 54 in FIG. 7.

An alternative form of a sensor 56 is illustrated in FIG. 8 and comprises a length of wire wrapped in a cylindrical form to provide a coil 80. The coil is electrically connected to the stylet in the same manner illustrated and described in regard to sensor 56 for delivering an electrical current to a signal generator. Preferably the length of wire is wrapped about an iron core thereby to increase the induced current in a manner well known in the art.

A cap 72 receives the proximal end of the stylet 68 as illustrated in FIG. 4. The stylet 68 extends along substantially the entire length of the lumen 40. The stylet 68 adds a desired degree of stiffness and rigidity to the catheter to facilitate the placement procedure. After placement of the catheter is completed, the cap is used for extracting the stylet 68 from the catheter body portion 12. The lumen 40 can then be used for the supply of nutrients or medication for the patient. The cap 72 is fitted to a cavity formed in a fixture 74 which is joined to the proximal end of the catheter which is opposite the distal end portion 14. The fixture 74 is provided with an additional duct section 76 having a removable closure cap 78 for access to the lumen when it is desired t o introduce fluids into the lumen of the catheter. It is also possible for a syringe to be connectable to the duct section 76 in a fluid tight manner, as is well known in the art, should it be desired to withdraw fluid from the lumen.

Figure 9:
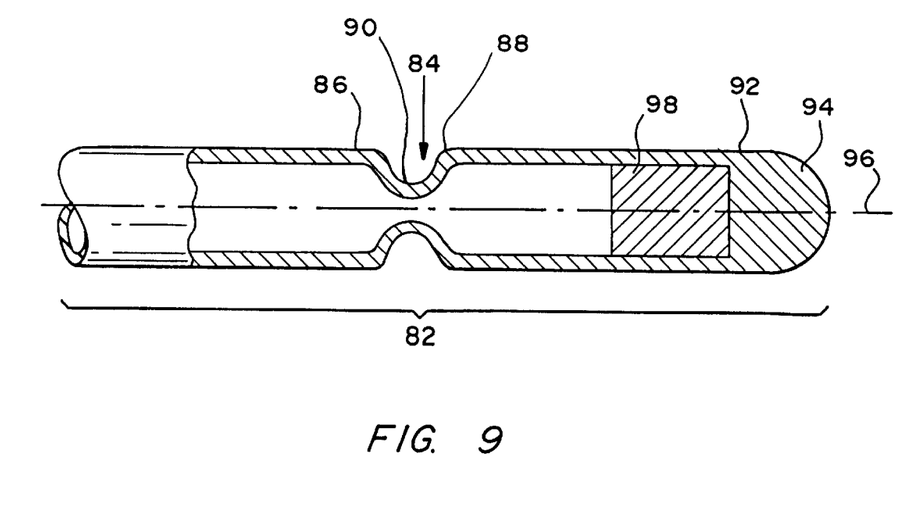
FIG. 9 is an enlarged sectional view of the distal end portion of a catheter according to the present invention which includes a waisted portion having a reduced cross-section for increased flexibility of a terminal end of the distal end portion and an asymmetrical projection for increased maneuverability of the terminal end.

An alternative embodiment of the catheter disclosed herein is illustrated in FIG. 9, showing distal end portion 82. The construction of the distal end portion 82 provides increased flexibility of one portion of the catheter as compared with the flexibility of an adjacent distal end portion of the catheter. In the depicted embodiment, the first portion of the distal end portion 14 of catheter 10 has a different diameter resulting in greater elasticity and thereby increased flexibility when compared to the adjacent distal end portion of catheter 10. Preferably the increased flexibility at the distal end of the catheter is provided by a waisted portion 84 extending along the distal end portion from a first location 86 to a second location 88. The waisted portion 84 has a reduced cross-sectional dimension at an intermediate location 90 with respect to the dimensions at the first and second locations 86 and 88. This results in increased flexibility of a terminal end portion 92 of the distal end portion 82 in comparison with a catheter having a similarly thick distal end portion of the same material in which the cross section dimension of the distal end portion remains unchanged throughout. Such increased flexibility provides increased maneuverability for the terminal end portion 92. If desired, more than one waisted portion 84 may be provided.

The distal end portion 82 illustrated in FIG. 9 provides a second feature for increasing the maneuverability of the distal end portion by providing a projection 94 which is asymmetrical with respect to a central axis 96 of the distal end portion 82. The projection 94 provides greater maneuverability due to its asymmetrical shape. That is, when projection 94 encounters a body surface, it will tend to be deflected more to one side due to its asymmetrical shape because of the unequal distribution of forces brought to bear upon the asymmetrical projection 94. In contrast, a symmetrical tip would realize an equal distribution of forces about its surface, thereby limiting the likelihood that the tip will be deflected upon contact with a body surface. The asymmetry of the projection 94 therefore is advantageous for increased maneuverability of the terminal end portion 92 during placement of catheter 10 through a patient's naris and gastrointestinal tract.

It is to be understood that the embodiment of the catheter illustrated in FIG. 9 may additionally include an insert 98 containing permanent magnets 44 or 50, as illustrated in FIGS. 5 and 6, ferromagnetic material 54, as illustrated in FIG. 7, or bits 70 of ferromagnetic material, as illustrated in FIG. 8. The distal end portion may also include sensor 56 as described hereinbefore.

The catheter also can include fiber optics, which, for example, may aid in selecting the position of the distal end portion of the catheter.

Methods of Use

The method for placing a catheter in a patient includes the step of providing a catheter constructed in accordance to the above-described embodiments of the apparatus. The method also includes the step of providing an external magnet. The catheter is positioned within a portion of a patient's body. The external magnet is brought into the proximity of the distal end portion of the catheter such that the sensor 56 provides a signal indicating that the needed magnetic coupling is present between distal end portion 14 of catheter 10 and the external magnet. The external magnet is then manipulated in order to position distal end portion 14 of catheter 10 at a preselected location within the patient's body. The external magnet is then moved away from the distal end portion 14 of catheter 10 and away from the patient. If a stylet is present in the catheter, the stylet is removed.

In alternative embodiments, the catheter disclosed herein may be adapted to other applications, with or without the use of the sensor. The catheters may be adapted for placement within the vasculature, such as arteries, as well as other body passages, such as ureters, urethras, gastrointestinal tubes, trachea, fallopian tubes, bile ducts, esophagus, and bronchi. These catheters can be adapted for localized delivery of therapeutic agents, such as for treatment of tumors or obstructive lesions; for angioplasty and angioscopy; for laser ablation, or for deployment of medical stents. In a preferred embodiment, the catheter has a distal end portion including a permanent magnetic or ferromagnetic material, which can be guided to selected positions within the vasculature of a patient using an external magnet. Such a catheter could readily be adapted by those of skill in the art for a variety of applications, such as those described in U.S. Pat. No. 5,476,450 to Ruggio (aspirating intravascular and cardiac obstructions) and U.S. Pat. No. 4,913,142 to Kittrell, et al. (laser angiosurgery).

Publications cited herein and the material for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:
1. A catheter system comprising
   a catheter having a distal end portion,
   a sensor provided at the distal end portion, and
   a magnetically responsive element selected from the group consisting of permanent magnets and ferromagnetic materials, provided at the distal end,
   wherein the sensor provides a signal in response to a magnetic field or magnetic flux, from a magnet, of a magnitude sufficient to ensure that the magnetically responsive element is magnetically coupled to the magnet positioned external a patient's body when the distal end portion of the catheter is inside the body of the patient.
2. The catheter system of claim 1 further comprising an indicator in communication with the sensor, wherein the indicator provides a second signal when triggered by the sensor's signal.
3. The catheter system of claim 2 wherein the indicator comprises a visible, audible, or tactile signal means.
4. The catheter system of claim 1 wherein the magnetically responsive element is a permanent magnet on the distal end portion of the catheter.
5. The catheter system of claim 4 wherein the permanent magnet has an elongated cylindrical shape having hemicylindrical magnetic pole faces.
6. The catheter system of claim 4 wherein the permanent magnet has an elongated cylindrical shape having planar pole faces at its terminal ends.
7. The catheter system of claim 1 further comprising an external magnet.
8. The catheter system of claim 1 wherein the distal end portion comprises a portion constructed of a ferromagnetic material.
9. The catheter system of claim 8 wherein the ferromagnetic material portion comprises a tubular member constructed of the ferromagnetic material.
10. The catheter system of claim 1 wherein the catheter defines a lumen extending along a length of the catheter, and wherein the catheter system further comprising a stylet for removable placement within the lumen.
11. The catheter system of claim 8 wherein the sensor is mounted on a distal end portion of the stylet.
12. The catheter system of claim 10 further comprising an indicator electrically connected to the sensor with the stylet, wherein the indicator provides a second signal when triggered by the sensor.
13. The catheter system of claim 12 wherein the stylet is constructed of an electrically conductive material.
14. The catheter system of claim 12 wherein the stylet comprises an electrical wire running along a length of the stylet.
15. The catheter system of claim 1 wherein the distal end portion includes a first portion exhibiting increased flexibility as compared with the flexibility of a second, adjacent portion of the distal end portion.
16. The catheter system of claim 15 wherein the first portion has a reduced cross-sectional dimension relative to a cross-sectional dimension of the second, adjacent portion.
17. The catheter system of claim 1 wherein the distal end portion further comprises a projection extending from the catheter, the projection having a configuration asymmetrical with respect to the longitudinal axis of the catheter.
18. The catheter system of claim 1 wherein the sensor is integral with or attached to the catheter.
19. The catheter system of claim 1 wherein the sensor comprises a housing containing electrically conducting reeds having a predetermined elasticity such that the electrical state of the sensor changes in response to the presence of the magnetic field or magnetic flux at a predetermined threshold level.
20. The catheter system of claim 19 wherein the electrical reeds are forced into contact with one another in the presence the magnetic field or magnetic flux at the predetermined threshold level, thereby allowing electricity to flow through the sensor.
21. The catheter system of claim 1 wherein the catheter is a duodenal catheter positionable within a patient's duodenum.
22. The catheter system of claim 1 wherein the catheter is a vascular catheter positionable within a patient's vasculature.
23. A method for intubating a patient, the method comprising:
   (a) providing a catheter having a distal end portion and comprising
      a sensor provided at the distal end portion and
      a magnetically responsive element selected from the group consisting of permanent magnets and ferromagnetic materials, provided at the distal end,
      wherein the sensor provides a signal in response to a magnetic field or magnetic flux, from a magnet, of a magnitude sufficient to ensure that the magnetically responsive element is magnetically coupled to the magnet positioned external a patient's body when the distal end portion of the catheter is inside the body of the patient;

(b) providing the external magnet;

(c) placing the distal end portion of the catheter inside the body of a patient;

(d) placing the external magnet in a position that is external to the body of the patient and proximate to the sensor;

(e) confirming the proximity of the external magnet and the distal end portion by monitoring the signal provided by the sensor; and (f) manipulating the external magnet to position the distal end portion of the catheter at a selected location within the body of the patient.

24. The method of claim 23 wherein the distal end portion includes a ferromagnetic material.

25. The method of claim 23 wherein the magnetically responsive element is a permanent magnet.

26. The method of claim 23 wherein the distal end portion includes a first portion exhibiting increased flexibility as compared with the flexibility of a second, adjacent portion of the distal end portion.

27. The method of claim 26 wherein the first portion has a reduced cross-sectional dimension relative to a cross-sectional dimension of the second, adjacent portion.

28. The method of claim 23 wherein the distal end portion further comprises a projection extending from the catheter, the projection having a configuration asymmetrical with respect to the longitudinal axis of said catheter.

29. The method of claim 23 wherein the distal end portion of the catheter is placed inside the gastrointestinal tract of a patient in step (c).

30. The method of claim 23 wherein the distal end portion of the catheter is placed inside the vasculature of a patient in step (c).

31. A catheter system for intubation of a patient, comprising a catheter having a distal end and suitable for duodenal insertion, a permanent magnet provided at the distal end, a sensor provided at the distal end, wherein the sensor comprises a housing containing electrically conducting reeds having a predetermined elasticity such that the electrical state of the sensor changes in response to the presence of a magnetic field or magnetic flux at a predetermined threshold level, thereby providing a first signal indicating said presence, and an indicator in communication with the sensor, wherein the indicator provides an audio, visual, or tactile second signal when triggered by the first signal.

32. The catheter system of claim 31 further comprising an external magnet which generates the threshold level of the magnetic field or magnetic flux.

* * * * *